United States Patent [19]

Brown et al.

[11] Patent Number: 5,583,259
[45] Date of Patent: Dec. 10, 1996

[54] 2-(RO)-1-(R) ETHYLAMINES

[75] Inventors: Eric Brown; Joël Touet, both of Le Mans; Jean-Pierre Le Goff, Mayenne Cedex, all of France

[73] Assignee: Les Laboratoires Beecham S.A., France

[21] Appl. No.: 436,915

[22] Filed: May 8, 1995

Related U.S. Application Data

[63] Continuation of Ser. No. 98,285, filed as PCT/EP92/00300, Feb. 7, 1992, abandoned.

[30] Foreign Application Priority Data

Feb. 8, 1991 [FR] France .................... 91 01451

[51] Int. Cl.$^6$ ................................ C07C 217/10
[52] U.S. Cl. ............................................ 564/346
[58] Field of Search ................................ 564/346

[56] References Cited

U.S. PATENT DOCUMENTS

| | | | |
|---|---|---|---|
| 4,863,935 | 9/1989 | Shida et al. | 514/332 |
| 5,266,599 | 11/1993 | Aubard et al. | 514/651 |
| 5,494,926 | 2/1996 | Owens et al. | 514/364 |

FOREIGN PATENT DOCUMENTS

| | | |
|---|---|---|
| 0000745 | 2/1979 | European Pat. Off. . |
| 2107926 | 5/1972 | France . |

OTHER PUBLICATIONS

Bjornholm et al, JACS, vol. 110 (1988) pp. 3862–3869.
Ojima et al, JACS, vol. 109 (1987) pp. 1798–1805.
Chang et al, J. Org. Chem., vol. 55 (1990) pp. 3475–3483.
Williams et al., J. Org. Chem., vol. 52 (1987) pp. 2615–2617.
RTECS Abstracts of J. Pharm. and Exp. Therapeutics (1990).
Shirlin et al., Chemical Abstracts, vol. 117 (1992) 251790m.
Owens et al., Chemical Abstracts, vol. 119 (1993) 8484g.
Johnson et al, J. Org. Chem., vol. 8 (1943) pp. 7–9.

*Primary Examiner*—Richard L. Raymond
*Attorney, Agent, or Firm*—Mary E. McCarthy; Stephen Venetianer; Edward T. Lentz

[57] ABSTRACT

A compound of formula (I), or a salt or solvate thereof,

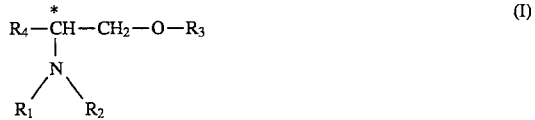

in which $R_1$ and $R_2$ each independently represents hydrogen, alkyl, optionally substituted aryl or optionally substituted aralkyl; $R_3$ represents alkyl, optionally substituted aryl or optionally substituted aralkyl and $R_4$ represents alkyl or optionally substituted aryl; a process for preparing such compounds and the use of such compounds for resolving certain racemates.

8 Claims, No Drawings

2-(RO)-1-(R) ETHYLAMINES

This is a continuation of application Ser. No. 08/098,285, filed Aug. 4, 1993, now abandoned, which is a 371 of PCT/EP92/00300, filed Feb. 7, 1992.

The present invention relates to novel compounds which are useful resolving agents for certain racemates, especially for DL-N-acetyl-4-hydroxyphenylglycine (hereinafter DL-N-acetyl-4-HPG) or DL-N-haloacetyl-4-HPG. The invention also relates to a process for effecting resolution of such racemates, especially for resolving DL-N-acetyl-4-HPG and DL-N-haloacetyl-4-HPG.

U.S. Pat. No. 3,869,505 discloses the preparation of DL-N-acetyl-4-HPG, and its use in resolving DL-2-(4-hydroxyphenyl)-glycine (hereinafter DL-2-4-HPG) into its optical isomers. The D(−) form of the latter is particularly useful in the preparation of penicillin and cephalosporin derivatives.

A group of novel compounds has now been discovered which has particular utility in the resolution of DL-N-acetyl-4-HPG or DL-N-haloacetyl-4-HPG into their (D−) forms, each of which can then be converted in known manner to the (D−) form of DL-2-4-HPG. These novel compounds may also be effectively used in the resolution of other acidic racemates.

According to the present invention, there is provided a compound of formula (I), or a salt or solvate thereof,

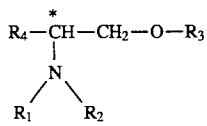   (I)

in which $R_1$ and $R_2$ each independently represents hydrogen, alkyl, optionally substituted aryl or optionally substituted aralkyl; $R_3$ represents alkyl, optionally substituted aryl or optionally substituted aralkyl and $R_4$ represents alkyl or optionally substituted aryl.

Suitably, $R_1$ and $R_2$ each independently represent hydrogen or alkyl.

Favourably, $R_1$ is hydrogen.

Favourably, $R_2$ is hydrogen.

Preferably, $R_1$ and $R_2$ each represent hydrogen.

Suitably, $R_3$ is an optionally substituted aralkyl group, such as an optionally substituted phenyl $C_{1-6}$ alkyl group, for example an optionally substituted benzyl group.

It is preferred if the aralkyl group is substituted in the aryl moiety.

Suitable substituted aralkyl groups include mono-halo and bis-halo substituted aralkyls, in particular 4-halo and 2,4-halo substituted aralkyl groups.

Examples of substituted aralkyl groups include 4-chlorobenzyl, 4-bromobenzyl and 2,4-dichlorobenzyl.

An example of an unsubstituted aralkyl group is a benzyl group.

Suitably, $R_4$ is an alkyl group; especially a $C_{1-6}$ alkyl group.

Preferably, $R_4$ is an ethyl group.

One preferred sub-group of compounds of formula (I) is a compound of formula (II), or a salt or solvate thereof,

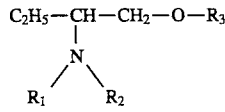   (II)

in which each of $R_1$ and $R_2$ is hydrogen, $C_{1-6}$ alkyl, optionally substituted phenyl or optionally substituted phenyl $C_{1-6}$ alkyl; and $R_3$ is optionally substituted phenyl or optionally substituted phenyl $C_{1-6}$ alkyl.

A particularly preferred sub-group of the compounds of formula (I) has the formula (III);

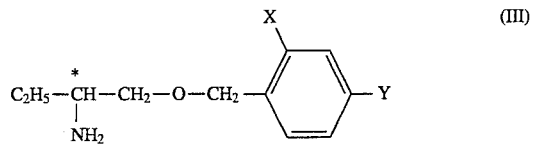   (III)

in which each of X and Y represents halogen, preferably chlorine.

The carbon atoms in the above formulae annotated with an asterisk (*) are chiral carbons. The compounds of formula (I) (and thus (II) and (III)) can therefore exist in one of two enantiomeric forms. The present invention extends to single isomers, including enantiomers, of formula (I) as well as to mixtures thereof, including racemates.

Preferably the compounds of formula (I) are in the form of an optically pure enantiomer.

Thus in one aspect the present invention provides a compound of formula (I), or a salt or solvate thereof, in the form of a single enantiomer. One form is the (R) enantiomer. One form is the (S) enantiomer.

Specific compounds of the invention are;
(R)-(−)-2-amino-1-(2,4-dichlorobenzyloxy)butane;
(R)-(−)-2-amino-1-benzyloxybutane;
(R)-(−)-2-amino-1-(4-chlorobenzyloxy)butane;
(R)-(−)-2-amino-1-(4-bromobenzyloxy)butane; and
S-(+)-2-amino-1-(4-chlorobenzyloxy)butane.

Examples of salts of the compounds of the invention are acid addition salts with conventional acids such as hydrochloric or maleic acids.

An example of a solvate is a hydrate.

When used herein the term 'alkyl' (whether used alone or when used as part of another group for example as in an 'aralkyl' group) includes straight and branched chain alkyl groups, containing from 1 to 12 carbon atoms, suitably 1 to 6 carbon atoms, for example methyl, ethyl, propyl or butyl.

When used herein the term 'aryl' (whether used alone or when used as part of other groups for example as in an 'aralkyl' group) includes phenyl and naphthyl optionally substituted with up to five, preferably up to three, groups selected from halogen, alkyl, phenyl, alkoxy, hydroxy, amino, nitro, alkoxycarbonyl, alkoxycarbonylalkyl, alkylcarbonyloxy, or alkylcarbonyl groups.

A preferred aryl group is a phenyl group.

A preferred substituent for an aryl group is halo.

The compounds of formula (I) may be prepared by reacting a compound of formula (IV)

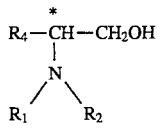   (IV)

in which $R_1$, $R_2$ and $R_4$ are as defined in formula (I), with a compound of formula (V):

Hal-$R_3$   (V)

in which Hal is halogen, preferably chlorine, and $R_3$ is as defined in formula (I); and thereafter, if required, preparing a salt or solvate of the compound of formula (I).

Preferably, the compound of formula (IV) is treated with a base, such as sodium hydride prior to reaction with compound (V).

Most preferably, for the preparation of single enantiomers of the compounds of formula (I), the compound of formula (IV) is also in the form of a single enantiomer: The chirality of the asterisked carbon in the compound of formula (IV) being the same as that in the required compound of formula (I).

The compounds of formulae (IV) and (V) are known commercially available compounds, or can be prepared from known compounds by known methods, e.g. as in U.S. Pat. No. 2,174,242 or J. Org. Chem. 8, 7, (1943).

The invention further provides a process for the resolution of an acidic racemate into individual enantiomers, which process comprises:

(i) preparing diastereomeric salts from the acidic racemate and a single enantiomer of a compound of formula (I) or a salt or solvate thereof;

(ii) separating the diastereomeric salts; and (iii) preparing an individual enantiomer of the acidic racemate from a diastereomeric salt.

The preparation of the diastereomeric salts may be carried out in any suitable solvent, generally an organic solvent such as isopropyl alcohol, at any convenient temperature, but generally at an elevated temperature.

The separation of the diastereomeric salts may be carried out by use of any conventional method, such as fractional crystallization. One preferred method involves seeding the mixture with the required salt to facilitate separation and especially to facilitate crystallizastion.

An enantiomer may be prepared from a diastereomeric salt by any conventional means. One suitable method involves treating the salt with a base and then separating the individual enantiomer of the starting racemate and the isomer of the compound of formula (I), for example by solvent extraction.

Generally, the isomer of the compound of formula (I) is recovered and then reused in the process.

The individual enantiomer of the starting racemate may be further purified by recrystallisation, if and as required.

Generally, the acidic racemate is an amino acid racemate, favourably an N-acyl amino acid.

One preferred racemate is DL-N-acetyl-4-hydroxyphenylglycine.

One preferred racemate is DL-N-haloacetyl-4-hydroxyphenylglycine.

Thus, in one preferred aspect the invention provides the preparation of DL-N-acetyl-4-HPG or DL-N-haloacetyl-4-HPG in optically active D(−) form, which comprises treating either compound, in solution, with a compound of formula (I), or a salt or solvate thereof, to prepare the mixture of diastereoisomeric salts, allowing the diastereoisomeric salt containing the optically active D(−) form the D(−) containing salt) to precipitate out, treating the D(−) containing salt with base, and separating the precipitated D(−) form from the solution.

Preferably, the DL-starting material is dissolved in an organic solvent, such as ethanol, at elevated temperature, the single stereoisomer of a compound of a compound of formula (I), or a salt or solvate thereof, is added, and the solution allowed to cool to room temperature after seeding with pure D(−) containing salt which is then used to provide the required optically active D(−) form.

The pure D-(−)-N-acetyl-4-HPG may be converted to D(−)2-4-HPG by conventional deacylation procedures, for example those disclosed in 'Protective Groups in Organic Chemistry' by J. F. W. McOmie, Plenum Press, London and New York, 1973 or French Patent No. 2107926.

The invention is illustrated by the following Examples:

EXAMPLE 1

Preparation of (R)-(−)-2-Amino-1-(2,4-dichlorobenzyloxy)butane

Pure (R)-(−)-2-amino-1-butanol (34.1 g) is treated with sodium hydride (11 g) in toluene (375 ml) by refluxing for 4 hours. 2,4-Dichlorobenzylchloride (75 g) is added to the reaction mixture and refluxed for a further 4 hours. The mixture is then cooled and 1M hydrochloric acid (900 ml) is added.

The aqueous layer is separated and made alkaline by addition of 1M sodium hydroxide solution (600 ml) Methylene dichloride (500 ml) is added to the aqueous layer and the organic and aqueous phases are separated. The organic phase is concentrated and distilled in order to obtain the pure product. Yield 70%.

$[\alpha]^{20}D = -12.5°$ (C 2.84 EtOH)

EbO,1=120°

$IR_{vmax}$ (film): 3376 (N=H) et 1093 (C—O—C) cm$^{-1}$ NMR (CDCl$_3$) δ (ppm): 7.5 (3H.m): 4.6 (2H, s): 3.5 (2H.m): 3.0 (1H, m): 1.45 (4H, m): 1.0 (3H, t).

Elemental microanalysis (as the hydrochloride) (C$_{11}$H$_{16}$Cl$_3$NO): Calc. % C46.42 H 5.67 N 4.92 O 5.62 Found % 46.60 5.76 5.01 5.84

EXAMPLES 2–4

The following compounds were then prepared using an analogous procedure to that described for the preparation of Example 1:

EXAMPLE 2

R-(−)Amino-1-benzyloxybutane;

$IR_{vmax}$ (film): 3400 (δNH): 1102 (C—O—C); 856 (NH) and 740; 699 (aryl) cm$^{-1}$ NMR (CDCl$_3$) δ (ppm): 7.33 (5H, s); 4.5 (2H, s); 3.3 (2H, m); 2.85 (1H, m); 1.3 (4H, m); 0.9 (3H, t).

Elemental microanalysis (as the hydrochloride) (C$_{11}$H$_{18}$ClNO): Calc. %: C 61.24 H 8.40 N 6.59 O 7.41 Found % 61.02 8.57 6.65 7.66

EXAMPLE 3

R-(−)-2-Amino-1-(4-chlorobenzyloxy)butane:

$IR_{vmax}$ (film): 3376 (N—H) and 1093 (C—O—C) cm$^{-1}$ NMR (CDCl$_3$) δ(ppm) 7.33 (4H, s); 4.5 (2H, s); 3.35 (2H, m); 2.9 (1H, m); 1.33 (4H, m); 0.9 (3H, t).

Elemental microanalysis (as the hydrochloride) (C$_{11}$H$_{17}$Cl$_2$NO): Calc% C 52.81 H 6.85 N 5.60 Found % 52.58 6.68 5.66

EXAMPLE 4

R-(−)-2-Amino-1-(4-bromobenzyloxy)butane $IR_{vmax}$ (film): 3376 (N—H) and 1093 (C—O—C) cm$^{-1}$ NMR (CDCl$_3$) δ(ppm): 7.55 (2H. d. J=8.5 Hz): 7.25 (2H, d, J=8.5 Hz); 4.5 (2H, s); 3.35 (2H, m); 2.9 (1H, m); 1.33 (4H, m); 0.9 (3H, t).

Elemental microanalysis (as the hydrochloride) (C$_{11}$H$_{17}$ClBrNO): Calc.% C 44.84 H 5.81 Cl 12.03 Br 27.12 N 4.85 O 4.99 Found % 45.17 5.72 12.19 27.15 4.85 5.43

EXAMPLE 5

S(+)-2-Amino-1-(4-chlorobenzyloxy)butane

The title compound was prepared using an analogous procedure to that described in Example 1, starting from S(+)-2-amino-1-butanol.

$IR_{vmax}$ (film); 3376 (N—H) and 1093 (C—O—C) $cm^{-1}$
NMR ($CDCl_3$) δ(ppm) 7.33 (4H, s); 4.5 (2H, s); 3.35 (2H, m); 2.9 (1H, m); 1.33 (4H, m); 0.9 (3H, t).

Elemental microanalysis (as the hydrochloride) ($C_{11}H_{17}Cl_2NO$): Calc. % C 52.81 H 6.85 N 5.60 O 6.40 Found % 53.25 6.94 5.55 6.33

EXAMPLE 6

Resolution of DL-N-acetyl-4-HPG

DL-N-acetyl-4-HPG is prepared according U.S. Pat. No. 3,869,505, and 50 g of this are dissolved in isopropyl alcohol (1000 ml) at elevated temperature.

(R)-(−)-2-amino-1-(2,4 dichlorobenzyloxy)-butane [(−)ADCBB] (60 g) as prepared in Example 1, are added with stirring, the mixture is seeded with pure D-(−)-N-acetyl-4-HPG, (−)ADCBB salt and allowed to cool to room temperature. After standing at room temperature overnight, the precipitate formed is collected by filtration and washed with isopropyl alcohol. After drying, 50.9 g of D-(−)-N-acetyl-4-HPG, (−)ADCBB salt are obtained. Yield=93% $[a]^{24}$=89.6% (Cl EtOH 95°) The salt is then dissolved in water by the addition of sodium hydroxide. The (−)ADCBB base is recovered by separation and distillation of the organic upper layer. The D-(−)N-acetyl-4-HPG is precipitated from the aqueous layer by neutralizing this layer with hydrochloric acid. After filtration and drying 44.1 g of pure D-(−)-N-acetyl-4-HPG are obtained, yield=95%. $[a]^{20}_D$=−214.9° (Cl 1.02, EtOH 95°)

The resolving agent is recovered as the hydrochloride or free base, according to the medium used.

EXAMPLE 7

Resolution of DL-N-chloroacetyl-4-HPG

According to the method of Example 6, the D-(−) form of the above was achieved in the indicated yields, using the following resolving agents

| | |
|---|---|
| (R)-(−)-2-amino-1-benzyloxybutane | yield = 75%. |
| (R)-(−)-2-amino-1-para-chlorobenzyloxybutane | yield = 53%. |
| (R)-(−)-2-amino-para-bromo-1-benzyloxybutane | yield = 61%. |
| (R)-(−)-2-amino-1-(2,4 dichlorobenzyloxy)butane | yield = 66%. |

We claim:

1. A compound of formula (I), or a salt or solvate thereof,

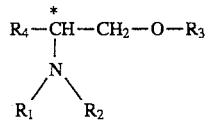

(I)

in which $R_1$ and $R_2$ each independently represents hydrogen, $C_{1-12}$-alkyl, optionally substituted aryl or aryl-$C_{1-12}$-alkyl optionally substituted in the aryl moiety; $R_3$ represents aryl-$C_{1-12}$-alkyl optionally substituted in the aryl moiety and $R_4$ represents $C_{1-12}$-alkyl or optionally substituted aryl; wherein any aryl group is a phenyl or naphthyl group optionally substituted with up to five groups selected from halogen, $C_{1-12}$-alkyl, phenyl, $C_{1-12}$-alkoxy, hydroxy, amino, nitro, $C_{1-12}$-alkoxycarbonyl, $C_{1-12}$-alkoxycarbonyl-$C_{1-12}$-alkyl, $C_{1-12}$-alkylcarbonyloxy or $C_{1-12}$-alkylcarbonyl; with the proviso that: (i) when $R_3$ is benzyl and $R_4$ is methyl, isopropyl, iso-butyl, phenyl or ortho-methoxyphenyl then one of $R_1$ and $R_2$ must represent $C_{1-12}$-alkyl, optionally substituted aryl or aryl-$C_{1-2}$-alkyl optionally substituted in the aryl moiety or (ii) when $R_3$ is benzyl substituted by $C_{1-12}$alkoxycarbonyl and $R_4$ is methyl, then $R_1$ and $R_2$ each independently represents hydrogen, optionally substituted aryl or aryl-$C_{1-12}$-alkyl optionally substituted in the aryl moiety.

2. A compound according to claim 1, wherein $R_1$ and $R_2$ each independently represent hydrogen or $C_{1-12}$-alkyl.

3. A compound according to claim 1, wherein $R_1$ and $R_2$ each represent hydrogen.

4. A compound according to claim 1, wherein $R_3$ is a benzyl group.

5. A compound according to claim 1, wherein $R_4$ is a $C_{1-12}$-alkyl group.

6. A compound according to claim 1 of formula (II), or a salt or solvate thereof,

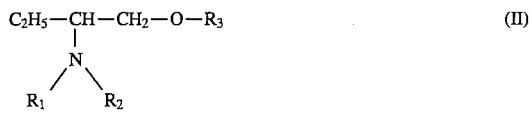

(II)

in which each of $R_1$ and $R_2$ is hydrogen, $C_{1-6}$ alkyl, optionally substituted phenyl or optionally substituted phenyl $C_{1-6}$ alkyl; and $R_3$ is optionally substituted phenyl $C_{1-6}$ alkyl.

7. A compound according to claim 1, or a salt or solvate thereof, in the form of an optically pure enantiomer.

8. A compound according to claim 1, selected from the group consisting of:

(R)-(−)-2-amino-1-(2,4-dichlorobenzyloxy)butane;

(R)-(−)-2-amino-1-benzyloxybutane;

(R)-(−)-2-amino-1-(4-chlorobenzyloxy)butane;

(R)-(−)-2-amino-1-(4-bromobenzyloxy)butane; and (S)-(+)-2-amino-1-(4-chlorobenzyloxy)butane; or a salt or solvate thereof.

* * * * *